(12) United States Patent
Scoggins

(10) Patent No.: US 9,410,072 B2
(45) Date of Patent: Aug. 9, 2016

(54) CEMENT RETARDER AND METHOD OF USING THE SAME

(75) Inventor: William Chrys Scoggins, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 759 days.

(21) Appl. No.: 13/172,534

(22) Filed: Jun. 29, 2011

(65) Prior Publication Data

US 2013/0000904 A1    Jan. 3, 2013

(51) Int. Cl.
| C09K 8/467 | (2006.01) |
| E21B 33/13 | (2006.01) |
| C04B 28/02 | (2006.01) |
| C04B 40/00 | (2006.01) |
| C07F 5/02 | (2006.01) |
| C04B 103/20 | (2006.01) |

(52) U.S. Cl.
CPC .............. *C09K 8/467* (2013.01); *C04B 28/02* (2013.01); *C04B 40/0039* (2013.01); *C07F 5/022* (2013.01); *E21B 33/13* (2013.01); *C04B 2103/20* (2013.01)

(58) Field of Classification Search
None
See application file for complete search history.

(56) References Cited

U.S. PATENT DOCUMENTS

| 3,053,674 | A | * | 9/1962 | Liberthson et al. ........... 106/717 |
| 3,234,154 | A | * | 2/1966 | Martin .............................. 524/8 |
| 3,254,719 | A | * | 6/1966 | Root ........................... 166/308.2 |
| 3,539,464 | A |   | 11/1970 | Harper et al. |
| 3,748,159 | A | * | 7/1973 | George et al. ................. 106/717 |
| 3,821,985 | A |   | 7/1974 | George |
| 3,856,541 | A | * | 12/1974 | Martin ........................... 106/717 |
| 4,034,038 | A | * | 7/1977 | Vogel ............................. 558/292 |
| 4,125,160 | A | * | 11/1978 | Crinkelmeyer et al. ....... 166/293 |
| 4,210,455 | A | * | 7/1980 | Metcalf et al. ................. 106/727 |
| 4,376,736 | A |   | 3/1983 | Stanley |
| 4,554,020 | A | * | 11/1985 | Hollenberg .................... 106/717 |
| 5,160,643 | A |   | 11/1992 | Dawson |
| 5,226,481 | A |   | 7/1993 | Le et al. |
| 5,273,580 | A | * | 12/1993 | Totten et al. ................... 106/724 |
| 5,322,124 | A |   | 6/1994 | Cowan et al. |
| 6,844,296 | B2 |   | 1/2005 | Dawson et al. |
| 6,978,835 | B1 |   | 12/2005 | Reddy et al. |
| 7,007,757 | B2 |   | 3/2006 | Gupta et al. |
| 7,067,000 | B1 |   | 6/2006 | Szymanski et al. |
| 7,288,147 | B2 |   | 10/2007 | Christensen et al. |
| 7,399,355 | B2 |   | 7/2008 | Szymanski et al. |
| 7,407,009 | B2 |   | 8/2008 | Santra et al. |
| 7,435,293 | B2 |   | 10/2008 | Caveny et al. |
| 7,527,098 | B2 |   | 5/2009 | Santra et al. |
| 7,794,537 | B2 |   | 9/2010 | Barlet-Gouedard et al. |
| 7,846,250 | B2 |   | 12/2010 | Barlet-Gouedard et al. |
| 7,922,808 | B2 |   | 4/2011 | Brower et al. |
| 2005/0166803 | A1 | * | 8/2005 | Dillenbeck et al. ........... 106/814 |
| 2008/0202752 | A1 | * | 8/2008 | Lopez et al. ................... 166/292 |
| 2008/0227667 | A1 |   | 9/2008 | Szymanski et al. |
| 2009/0107676 | A1 | * | 4/2009 | Saunders ....................... 166/293 |
| 2011/0028607 | A1 |   | 2/2011 | Morgan et al. |
| 2011/0108274 | A1 |   | 5/2011 | Caritey et al. |

FOREIGN PATENT DOCUMENTS

| CA | 1227505 | * | 9/1987 |
| EP | 0614859 A2 |   | 9/1994 |
| GB | 1134716 A |   | 11/1968 |
| GB | 2035992 A |   | 6/1980 |

* cited by examiner

*Primary Examiner* — Angela M DiTrani
*Assistant Examiner* — Anuradha Ahuja
(74) *Attorney, Agent, or Firm* — John Wilson Jones; Jones & Smith, LLP

(57) ABSTRACT

The reaction product of a polyhydroxy compound and borax is used as a cement retarder for slurries introduced into a wellbore. The molar ratio of the polyhydroxy compound to boron, derived from the borax, is from 1:1 to about 4:1. The polyhydroxy compound may be a sugar such as a gluconic acid, gluconate or glucoheptonate or a salt thereof.

32 Claims, 2 Drawing Sheets

CEMENT RETARDER AND METHOD OF USING THE SAME

FIELD OF THE INVENTION

The invention relates to a high temperature cement retarder and to a method of cementing a well with the cement retarder.

BACKGROUND OF THE INVENTION

Hydraulic cements are cements that set and develop compressive strength due to a hydration reaction, and thus can be set under water. Hydraulic cements are often used for cementing pipes or casings within a wellbore. Successful cementing of well pipe and casing during oil and gas well completion requires cementitious slurries to exhibit a pumpable viscosity, good fluid loss control, minimal settling of particles and the ability to set within a practical time at elevated temperatures.

In a typical completion operation, the cementitious slurry is pumped into the well, down the inside of the pipe or casing and back up the outside of the pipe or casing through the annular space. This process seals the subterranean zones (often referred to as "zonal isolation") in the formation and supports the casing. Under normal conditions, hydraulic cements, such as Portland cement, quickly develop compressive strength upon introduction to the well, typically within 48 hours from introduction. As time progresses, the cement develops greater strength while hydration continues.

It is common to use a retarder with the hydraulic cement in order to increase the pumping time of the cementitious slurry. In so doing, the retarder provides adequate thickening time to the cementitious slurry and thus enables placement of the slurry at its desired location. In order to minimize lost rig time, the thickening time of a cementitious slurry to attain a Bearden consistency (Bc) of 70 is most desirably from about 4 to about 5 hours.

In general, set retarders may be characterized as being low, medium or high temperature retarders depending on the bottom hole temperature encountered. In addition to increasing the pumping time of the cementitious slurry at elevated temperatures, the retarder also extends the setting time of the cementitious slurry.

Water-soluble sugars, sugar acids and their salts, borax and boric acid are known cement retarders. For instance, U.S. Pat. No. 3,100,526 discloses the use of glucoheptonic acid and salts thereof as a retarder; U.S. Pat. No. 3,053,673 discloses retarder systems containing a lignin derivative, such as a lignosulfonic acid salt, and either gluconic acid, gluconic acid delta lactone or an alkali metal, ammonium or alkaline earth metal gluconate; U.S. Pat. No. 4,065,318 discloses blends of borax, boric acid and gum arabic as retarders; U.S. Pat. No. 4,210,455 discloses set retarders of alkaline earth metal salts of sugar acids as well as alkaline earth metal salts of borate esters of sugars; and U.S. Pat. No. 4,706,755 discusses the use of borax as cement retarders.

Sugars have proven to be highly desirable as set retarders since they are environmentally safe. However, the use of sugars is restricted to low bottom hole temperatures since they break down at temperatures in excess of 250° F.

Boric acid and borax (also known as sodium tetraborate decahydrate, sodium tetraborate, sodium borate and disodium tetraborate) are considered high temperature retarders but are known to over-retard the cementitious slurry at lower temperatures. A slurry which is over-retarded contains too much retarder and thus takes a very long time to set. In some cases, an over-retarded cement slurry will not set at all. A slurry which is over-retarded increases the costs of cementing, including loss of rig time. For this reason, boric acid and borax are typically applied at high temperatures, generally in excess of 350° F.

In addition to over-retarding the slurry, boric acid and borax are not highly soluble in water at ambient temperatures. Thus, when a cementitious slurry is prepared on the fly, there typically is an abundance of non-dissolved, dispersed particulates of boric acid and borax in the slurry. When introduced downhole, shorter or uncontrolled set times and lost rig time are often seen since setting requires dissolution of the borax or boric acid in the slurry.

Further, boric acid set retarders usually contain boric acid or its equivalent in excess of 5.5%. Such amounts are in excess of established international thresholds of non-toxicity.

A need exists for a set retarder which may be applied over a broad temperature range and which does not over-retard the cementitious slurry introduced into the well.

A need further exists for a high temperature cement retarder which is both environmentally safe and environmentally friendly.

Further, a need exists for the development of a high temperature retarder which delays setting of a cement slurry at bottom hole temperatures in excess of 350° F.

SUMMARY OF THE INVENTION

A cement retarder which does not rapidly break down at temperatures above 250° F. may be formed by reacting a polyhydroxy compound and borax under controlled conditions. The polyhydroxy compound and borax forms a "complex" which is defined by boron being covalently bonded with one or more, preferably four, oxygens of the hydroxyl groups of the polyhydroxy compound and borate groups forming ionic bonds with sodium.

The disassociation temperature of the complex is greater than the disassociation temperature of the non-complexed polyhydroxy compound. Within the complex, the molecules of the polyhydroxy compound are placed into a fixed position by the borate groups. As the temperature downhole increases, the complex finally disassociates around 270° F. to render a high temperature set retarder; the disassociated complex releasing the polyhydroxy compound and various borate salts. Thus, the borate groups keep the polyhydroxy compound from breaking down at temperatures less than 270° F. and in turn, the polyhydroxy compound, by forming ester bonds with the borate groups, prevents these from over-retarding the slurry at lower temperatures. As such, the complex provides for the release of various borate salts at highly elevated temperatures.

The complex further may be formed in the presence of caustic or alkali hydroxide under controlled conditions. The sodium tetraborate in solution then reacts with the hydroxy groups of the polyhydroxy compound and, in light of the fact that it is a Lewis acid, links boron with oxygens of the hydroxy groups of the polyhydroxy compound. The reaction, where the polyhydroxy compounds are sugars and four oxygens are linked to one boron, may be represented by any of the following equations:

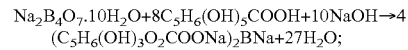

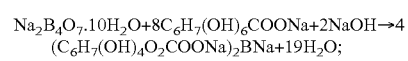

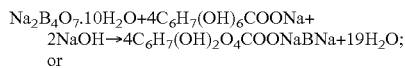

or

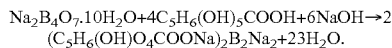

Since the borate salts form firm covalent bonds with the polyhydroxy compound, it may no longer pose a threat of over-retardation to the slurry. Further, lost rig time may be circumvented since dissolution of the borax or boric acid in the slurry is no longer a concern in light of the formation of the complex.

BRIEF DESCRIPTION OF THE DRAWINGS

In order to more fully understand the drawings referred to in the detailed description of the present invention, a brief description of each drawing is presented, in which.

DETAILED DESCRIPTION OF THE PREFERRED EMBODIMENTS

Figure 1:
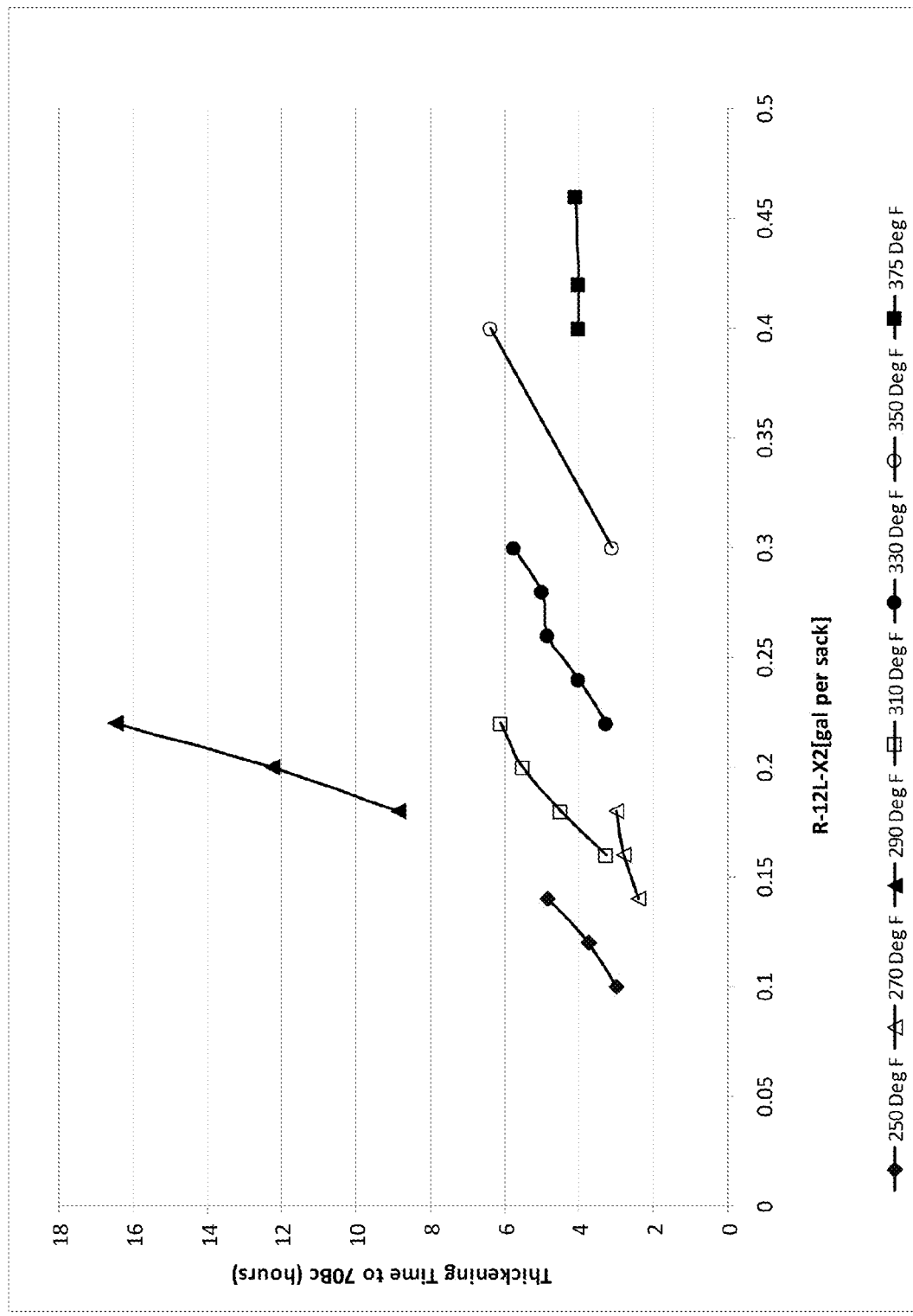
FIG. 1 shows the linear relationship of a boron/di-glucoheptonate complex at temperatures up to 375° F.

The cement set retarder is a borate ester complex formed from a polyhydroxy compound (low temperature cement retarder) and borate salts, such as sodium tetraborate (high temperature cement retarder). The borate ester complex is formed typically in the presence of an alkaline medium.

The polyhydroxy component of the complex as well as the borate portion of the complex are masked at lower temperatures. Thus, through the formation of borate ester bonds, the borate portion of the complex prevents the polyhydroxy compound from breaking down and the polyhydroxy compound prevents the borate from over-retarding at lower temperatures by keeping borate groups "fixed" or inactive within the complex. As the temperature to which the cement slurry is exposed reaches approximately 270° F., the complex breaks down, the polyhydroxy compound and the metaborate are released. The released metaborate may then retard the setting of the cement up to 350° F. and as high as 410° F. and above.

In an embodiment, the complex may be prepared by reacting stoichiometric quantities of borax, an alkali hydroxide and a polyhydroxy compound. The complex contains covalent bonds, formed between boron and the oxygens of the hydroxyl groups of the polyhydroxy compound, as well as ionic bonds, formed by the borate groups and sodium.

The molar ratio of polyhydroxy compound to boron in the cement retarder (derived from the borax), is from about 1:1 to about 4:1. In a preferred embodiment, the cement retarder defined herein may be made by reacting 4 to 8 moles of a polyhydroxy compound per 1 mole of borax in the presence of caustic to yield a complex which exhibits excellent cement retarding properties at temperatures as high as 400° F. and above.

The polyhydroxy compound may be a sugar, a sugar acid, a salt of a sugar acid, a glycol, polyvinyl alcohol, hydroxyethyl cellulose, carboxymethylhydroxyethyl cellulose, a starch, a galactomannase such as hydroxypropyl guar, or other natural or synthetic compounds containing multiple hydroxyl groups. Preferably, the polyhydroxy compounds contains vicinal hydroxy groups.

In a preferred embodiment, the polyhydroxy compound is a sugar. Most preferred are gluconic acid or a salt thereof, glucoheptonic acid, or a salt thereof. In a preferred embodiment, 4 to 8 moles of sodium glucoheptonate may be reacted with one mole of borax to yield a complex of the glucoheptonate and sodium tetraborate. A representative reaction between borax and sodium glucoheptonate to form a 1:1 dimer of glucoheptonate/borate may be illustrated as:

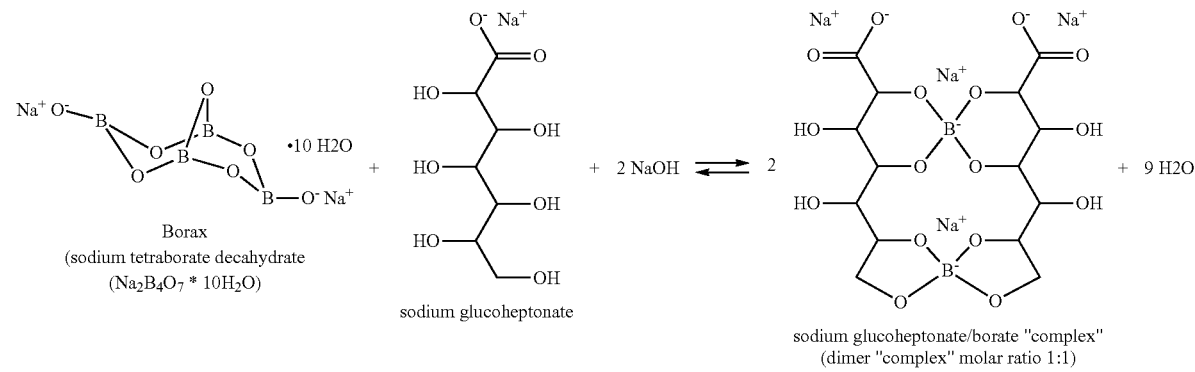

wherein the 1:1 molar ratio borate dimer may be prepared by reacting 1 mole of borax with 4 moles of sodium glucoheptonate in water in the presence of caustic. During the reaction, the pH of the solution drops and an alkaline medium, shown as sodium hydroxide, is added to increase the pH. Typically, the pH of the final reactant solution is between from about 8.0 to about 9.0. During the reaction, two borate groups form firm ester linkages to the two sugars thus preventing most vibrational, rotational and translational motion.

Restrictions on vibrational, rotational and translational motion are more pronounced when polymeric complexes are formed. For instance, under controlled reaction conditions 1 mole of borax may be reacted with 4 moles of sodium glucoheptonate in the presence of caustic to produce a polymeric complex having a 1:1 molar ratio between borate and sodium glucoheptonate:

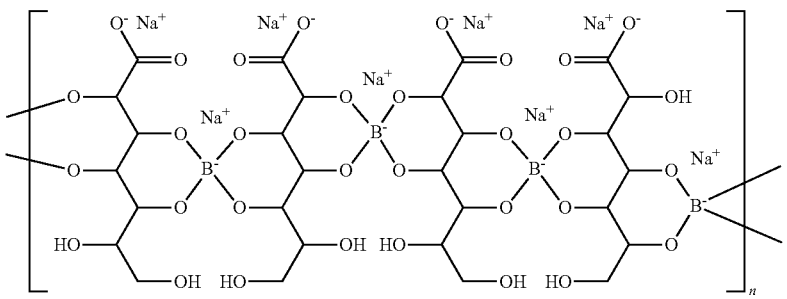

The polymeric complex may be formed by intra-, as well as, inter-molecular borate ester linkages and would be more favored for the 1:1 molar ratio of sugar to borate than the 2:1 ratio.

The process of elevated heat downhole causes an increase in various rotational, vibrational and translational motions of the functional groups of polyhydroxy compounds and their derivatives to be very rapid until the covalent bonds break. The breaking of the covalent bonds causes the polyhydroxy compound to lose its physical and chemical properties. When introduced in a non-complexed form, the polyhydroxy compound typically thermally degrades at a downhole temperature around 250° F. or greater. Such degradation is usually characterized by oxidation, dehydration and various other condensation reactions of the polyhydroxy compound, initially, especially between the vicinal —OH groups.

The cement retarder described herein puts the functional groups of the molecules of the polyhydroxy compounds into a fixed position by complexation or crosslinking of the metal borate. During solvation, the complex becomes surrounded by water molecules; the borate is then masked and is no longer capable of retarding the slurry. With an increase in temperature, the kinetic energy of the complex increases and degrades, thus breaking apart to form $BO_2^-$ anions (metaborates) in-situ which then retard the cementitious slurry. Under some experimental conditions, the molar ratio of polyhydroxy compound to metaborate in the disassociated product may range from 1:1 to 2:1. For instance, the molar ratio of sodium glucoheptonate and sodium metaborate in the disassociated product may be 1:1 to 2:1 and the molar ratio of gluconic acid or gluconic acid salt to sodium metaborate in the disassociated product may be 2:1.

Thermal degradation of the polymeric glucoheptonate/borate "complex" may be illustrated as:

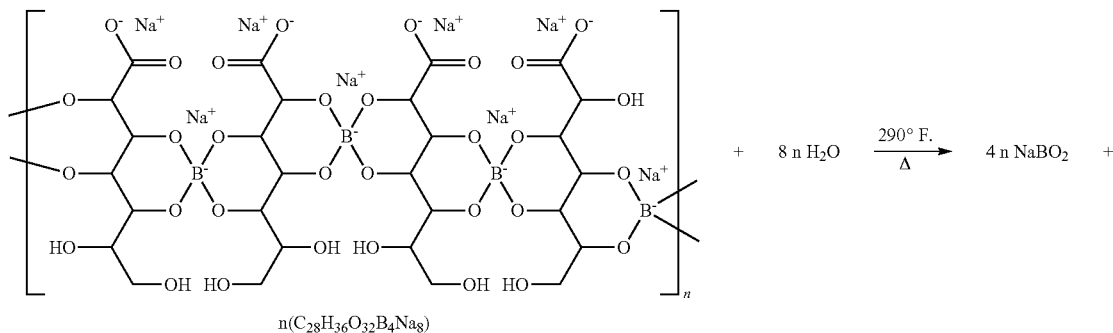

$n(C_{28}H_{36}O_{32}B_4Na_8)$

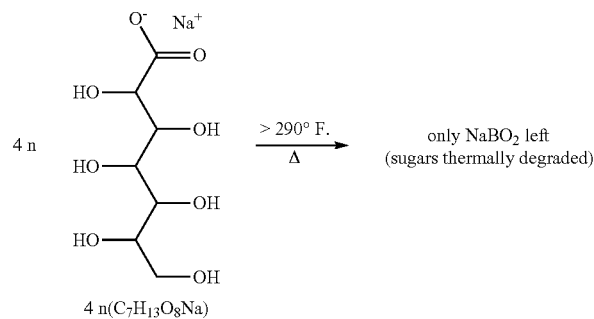

$4\,n(C_7H_{13}O_8Na)$ wherein at 290° F., the complex has been broken down into units of sodium glucoheptonate and sodium metaborate. At temperatures in excess of 290° F., the sugars are thermally degraded and only sodium metaborate remains.

Thus, the life expectancy of the sugar molecules increase dramatically, even at very high temperatures. Along with the polyhydroxy compound, the other portion of the complex, i.e., sodium metaborate, exhibits cement retardation properties. The breaking of the "complex" at very high temperatures provides for the release of retarder at very high temperatures.

The "complex" described herein is particularly advantageous since it is environmentally friendly. For instance, the components of the complex have been released for usage in the North Sea.

Whereas borax per se is considered a more-or-less efficient high temperature cement retarder, its low solubility in water at room temperature of only 2.5% restricts its application greatly since it has to be added as a powder or suspension. When added as a suspension, its effectiveness is dependent on its rate of solvation. This causes concern due to the danger of under-retardation and over-retardation. In addition, the recently established international threshold of toxicity (Rep. Cat. 2; R-60-61) for borax indicates that any retarder or blend of retarders with a borax concentration greater than 8.5 wt. % must be labeled as being toxic and possibly damaging to the human embryo. This greatly restricts its application. In contrast, the complex defined herein is readily soluble in water, readily biodegradable and non-bioaccumulating as well as non-toxic in the retarder formulation since the concentration of borax is below 8.5%. Typically, the retarder formulated with the complex defined herein contains between 1.80%-3.42% of borax equivalent.

The complex defined herein is a broad-range retarder and thus may be applied at a much broader temperature range by, for instance, changing the quantities of the polyhydroxy compound and borax. Being a broad-range retarder, the "complex" retards settling of slurries at temperatures from 200° F. to in excess of 400° F. while showing a linear relationship between the thickening time (TT) of the slurry and the quantity of composite in the cementitious slurry. For instance, by changing the dosage of the retarder in the slurry, it can prolong the setting of cement slurries at temperatures from 250° F. to about 410° F.

The complex is formed typically in the presence of an alkaline medium. The alkaline medium may be formed from such caustic as sodium hydroxide, potassium hydroxide, lithium hydroxide or cesium hydroxide, though typically is sodium hydroxide. Typically the molar ratio of caustic to sodium tetraborate is from about 1:1 to about 10:1, preferably from about 1:1 to about 6:1. This is dependent on whether the sugar acid is added as a salt or as the free acid.

The complex may further be used in combination with a conventional low, moderate or high temperature cement retarder in order to attain a very broad range cement retarder for low, medium and high temperatures. When used, the conventional cement retarder is preferably a low to moderate temperature cement retarder. In a preferred embodiment, the low to moderate temperature cement retarder is a lignin sulfonate, such as a sodium lignosulfonate, calcium lignosulfonate, etc. When present, the weight ratio of conventional cement retarder to complex is typically from 2 to about 6. In a preferred embodiment, the conventional cement retarder is a conventional low to moderate temperature cement retarder and the complex is the reaction product of sodium glucoheptonate and sodium tetraborate. Suitable weight ratios include 2:1, conventional cement retarder to complex.

The set retarder is used with an aqueous slurry of cement for introduction into a gas or oil wellbore. Hydraulically-active cementitious materials, suitable for use in the cementitious slurry, include materials with hydraulic properties, such as hydraulic cement, slag and blends of hydraulic cement and slag (slagment), which are well known in the art. The term "hydraulic cement" refers to any inorganic cement that hardens or sets due to hydration. As used herein, the term "hydraulically-active" refers to properties of a cementitious material that allow the material to set in a manner like hydraulic cement, either with or without additional activation. Hydraulically-active cementitious materials may also have minor amounts of extenders such as bentonite, gilsonite, and cementitious materials used either without any appreciable sand or aggregate material or admixed with a granular filling material such as sand, ground limestone, the like. Strength enhancers such as silica powder or silica flour can be employed as well. Hydraulic cements, for instance, include Portland cements, aluminous cements, pozzolan cements, fly ash cements, magnesia cements (Sorel cements) and the like. Thus, for example, any of the oil well type cements of the class "A-H" as listed in the API Spec 10, (1st ed., 1982), are suitable hydraulic cements. In addition, the cementitious material may include silica sand/flour and/or weighing agents including hematite or barite.

Mixing water is utilized with the dry cement composition to produce a fluid pumpable slurry of suitable consistency. API Spec 10, Second Edition, June 1984 which is known in the cement industry, describes an approved apparatus and method for measuring the consistency of cement slurries in terms of Bearden consistency (Bc). A pumpable slurry should measure in the range from about 2-20 Bc and preferably be in the range from about 5 to 11 Bc. Slurries thinner than about 5 Bc will tend to have greater particle settling and free water generation. Slurries thicker than about 20 Bc become increasingly difficult to mix and pump.

Depending upon the particular slurry and intended conditions of use, mixing water is utilized in the slurry of the present invention in the range from about 30 to 150 weight percent based upon the dry weight of cement and preferably is in the range of about 35 to 90 weight percent.

The cementitious slurry of the invention may further contain conventional additives used in the cementing of a gas or oil wellbore such as suspending or thixotropic agents, fluid loss control additives, strength retrogression additives, permeability reducers, weighting materials, permeability reducers and anti-settling agents, etc.

The set retarders employed in the cementitious slurries of the invention do not require an intensifier. In fact, the cementitious slurries typically exhibit retardation of set time at temperatures in excess of 400° F. If desired, intensifiers known in the art, such as those disclosed in U.S. Pat. No. 5,105,885, may be employed.

The set retarder is capable of delaying the set time of the cementitious composition until the slurry is placed into its desired location. When used, the set time of the aqueous slurry may be delayed until downhole temperatures as high as 410° F. are obtained. Thus, the aqueous slurry may be hardened to a solid mass at elevated temperatures within the wellbore. Further, the aqueous slurries used in the invention may exhibit set times at elevated temperatures even in the absence of an intensifier.

The following examples are illustrative of some of the embodiments of the present invention. Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

All percentages set forth in the Examples are given in terms of weight units except as may otherwise be indicated.

EXAMPLES

Example 1

A boron/di-gluconate complex (GLU-1) was prepared by mixing in a 250 ml flask, equipped with a magnetic stirrer, 200 g (0.51 mol) of gluconic acid solution (50% active) and 24.3 g (0.0637 mol) borax stirred until clear and left standing overnight. About 24 g of NaOH was then added and the mixture was allowed to cool. The pH of the mixture was recorded as 9.0. The density of the complex solution was 1.34 g/cm³ and the activity of the complex was about 48%. The reaction may be represented as:

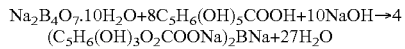

$Na_2B_4O_7 \cdot 10H_2O + 8C_5H_6(OH)_5COOH + 10NaOH \rightarrow 4(C_5H_6(OH)_3O_2COONa)_2BNa + 27H_2O$

Example 2

A boron/di-glucoheptonate complex (GLU-2) was prepared by mixing in a 250 ml flask, equipped with a magnetic stirrer, 200 g (0.24 mol) of sodium glucoheptonate solution (30% active) and about 11.5 g (0.0302 mol) borax stirred for about 30 minutes. About 1.7 g of NaOH was then added and the mixture was stirred for an additional 5 minutes. The pH of the mixture was recorded as approximately 8.0. The density of the complex was 1.18 g/cm³ and the activity of the complex was about 30%. The 2:1 molar reaction may be represented as:

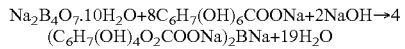

$Na_2B_4O_7 \cdot 10H_2O + 8C_6H_7(OH)_6COONa + 2NaOH \rightarrow 4(C_6H_7(OH)_4O_2COONa)_2BNa + 19H_2O$

Example 3

A boron/mono-glucoheptonate complex (GLU-3) was prepared by mixing in a 250 ml flask, equipped with a magnetic stirrer, 200 g (0.24 mol) of sodium glucoheptonate solution (30% active) and about 23.1 g (0.06 mol) borax stirred for about 10 minutes. About 1.7 g of NaOH was then added and the mixture was stirred for an additional 5 minutes. The pH of the mixture was recorded as approximately 8.0. The density of the complex was 1.21 g/cm³ and the activity of the complex was about 30%. The 1:1 molar reaction may be represented as:

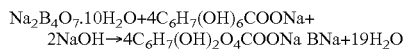

$Na_2B_4O_7 \cdot 10H_2O + 4C_6H_7(OH)_6COONa + 2NaOH \rightarrow 4C_6H_7(OH)_2O_4COONa\ BNa + 19H_2O$

Example 4

A boron/mono-gluconate complex (GLU-4) was prepared by mixing in a 250 ml flask, equipped with a magnetic stirrer, 200 g (0.51 mol) of gluconic acid solution (50% active) and 48.6 g (0.127 mol) borax stirred for about 5 minutes. About 16.9 g of NaOH was then added and the mixture was allowed to cool. The pH of the mixture was recorded as 7.0. The density of the complex was 1.33 g/cm³ and the activity of the complex was about 47%. The reaction may be represented as:

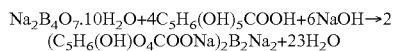

$Na_2B_4O_7 \cdot 10H_2O + 4C_5H_6(OH)_5COOH + 6NaOH \rightarrow 2(C_5H_6(OH)O_4COONa)_2B_2Na_2 + 23H_2O$

Examples 5-22

Cementitious slurries were prepared by mixing neat Class G Portland cement and fresh water at 14.6 pounds per gallon (ppg). To each slurry was added at room temperature an amount in gallons per sack of cement (gps):

35% weight percent silica flour;

0.1 gps FP-16LP, a defoamer;

0.4 gps FL-67LG, a fluid loss control additive;

1.2 gps BA-58L, a microsilica suspension bonding agent;

0.05 gps ASA-302L, an anti-settling agent; and

R-15L, a high temperature lignosulfonate cement retarder wherein FP-16L, FL-67L, BA-58L, ASA-302L, and R-15L are all products of Baker Hughes Incorporated.

The resultant slurries were maintained with occasional agitation. To each slurry was then added GLU-1 or GLU-2.

Standard API viscosity and fluid loss tests were conducted on the cement slurries; the viscosity being measured against industry standard torque measurement of 70/100 Bc (representing the amount of torque required to move the paddle through the cement slurry). The results are set forth in Table I. The thickening time (TT), representing the amount of time (hrs:minutes) that the slurry remained in a liquid state was then determined. For instance, the measurement 1:53 refers to the amount of time for the cement slurry to reach 70/100 Bc. The results are set forth in Table I:

TABLE I

| Ex. No. | GLU-1, Gps | GLU-2, gps | R-15L, gps | Temp, °F. | TT (hrs:mins) | R-15L:GLU-1/2 |
|---|---|---|---|---|---|---|
| Comp. 5 | | | 0.06 | 250 | 1:53 | |
| Comp. 6 | | | 0.10 | 250 | 3:22 | |
| Comp. 7 | | | 0.12 | 250 | 4:07 | |
| Comp. 8 | | | 0.15 | 250 | 11:28 | |
| 9 | 0.04 | | 0.12 | 250 | 23:01 | 3 |
| 10 | 0.02 | | 0.12 | 250 | 12:06 | 6 |
| 11 | 0.06 | | 0.12 | 260 | 17:26 | 2 |
| 12 | 0.04 | | 0.12 | 260 | 7:04 | 3 |
| 13 | 0.02 | | 0.12 | 260 | 5:16 | 6 |
| 14 | 0.04 | | 0.14 | 260 | 13:29 | 3.5 |
| 15 | 0.04 | | 0.12 | 270 | 3:03 | 3 |
| 16 | 0.05 | | 0.12 | 270 | 4:22 | 2.4 |
| 17 | 0.07 | | 0.12 | 270 | 37:49 | 1.7 |
| 18 | 0.05 | | 0.14 | 270 | 25:23 | 2.8 |
| 19 | | 0.04 | 0.12 | 260 | 8:42 | 3 |
| 20 | | 0.04 | 0.14 | 260 | 12:10 | 3.5 |
| 21 | | 0.04 | 0.16 | 260 | 51:53 | 4.0 |
| 22 | | 0.05 | 0.12 | 260 | 59:36 | 2.4 |

Table I illustrates GLU-1 to be an excellent retarder even at very small additions. GLU-2 rendered better results than GLU-1.

Examples 19-45

Cementitious slurries were prepared by mixing Class G Portland cement and fresh water at 14.6 ppg. To each slurry was added at room temperature 35 weight percent silica flour, 0.01 gps FP-16L G deformer, 0.40 gps FL-67L, 1.2 gps BA-58L, 0.05 gps ASA-302L and a mixture of 200 g R-12L and 100 g of GLU-2 (R-12L X2). (R-12L is a low to moderate temperature lignosulfonate cement retarder.) The thickening time (TT) data is set forth in Table II:

TABLE II

| Ex. No. | R-12LX2, gps | Temp, °F. | TT (hrs) |
|---|---|---|---|
| 23 | 0.10 | 250 | 3.0 |
| 24 | 0.12 | 250 | 3.75 |
| 25 | 0.14 | 250 | 4.83 |
| 26 | 0.14 | 270 | 2.4 |
| 27 | 0.16 | 270 | 2.8 |
| 28 | 0.18 | 270 | 3.0 |
| 29 | 0.18 | 290 | 8.86 |
| 30 | 0.20 | 290 | 12.25 |
| 31 | 0.22 | 290 | 16.45 |
| 32 | 0.16 | 310 | 3.25 |
| 33 | 0.18 | 310 | 4.5 |
| 34 | 0.20 | 310 | 5.5 |
| 35 | 0.22 | 310 | 6.1 |
| 36 | 0.22 | 330 | 3.25 |
| 37 | 0.24 | 330 | 4.0 |
| 38 | 0.26 | 330 | 4.83 |
| 39 | 0.28 | 330 | 5.0 |
| 40 | 0.30 | 330 | 5.75 |
| 41 | 0.30 | 350 | 3.11 |
| 42 | 0.40 | 350 | 6.4 |
| 43 | 0.40 | 375 | 4.0 |
| 44 | 0.42 | 375 | 4.0 |
| 45 | 0.46 | 375 | 4.1 |

The data of Table II is plotted in FIG. 1. As illustrated, at all temperature ranges there was almost a perfect linear relationship between the thickening time (TT) of the slurry and the quantity of R-12L-X2 added. Further, FIG. 1 shows that the low to moderate temperature lignosulfonate retarder starts to break down as the temperature of the cement retarder system (lignosulfonate+polymeric glucoheptonate/borate "complex") reaches 270° F. This can be seen by a decrease in thickening time at this temperature. As the temperature of the system is further increased, FIG. 1 shows a sudden increase in thickening time at 290° F. from 3 hours to 15 hours which indicates that the sodium gluconate/borate "complex" became thermally unstable and started to fall apart forming sodium borate ($NaBO_2$) and sodium glucoheptonate ($C_7H_{13}O_8Na$) which are both strong retarders and caused the system to have a much longer thickening time. Finally, above 290° F. the sodium glucoheptonate further degraded leaving only the sodium borate as the high temperature retarder component left in the system. This is illustrated by the system returning to "normal" thickening times of approximately 4 hours (and linear quantities of retarder added) even with increasing temperatures. FIG. 1 shows that the borate retarder stops working above 375° F. (slope of line approaching zero) which can be noticed by the slurry not being able to be retarded much over 4 hours, regardless of how much retarder was added.

Examples 46-77

Cementitious slurries were prepared by mixing neat Class G Portland cement and fresh water at 16.0 ppg. To each slurry was added at room temperature 0.01 gps FP-16LG, 0.08 gps CD-34L (a chemical dispersant of Baker Hughes Incorporated) and the combination of 200 g R-12L and 100 g of GLU-3 (R-12L X2B). A comparison between R-12-X2 and R-12L-X2B is shown in Table III:

TABLE III

| Temp, °F. | Gal/sk | R-12L-X2 70Bc TT (hrs) | R-12L-X2B 70Bc TT (hrs) |
|---|---|---|---|
| 270 | 0.18 | 21.86 | 10.06 |
| 290 | 0.18 | 12.96 | 6.56 |
| 310 | 0.18 | 5.36 | 3.25 |
| 350 | 0.4 | 6.4 | 6.4 |

The thickening time (TT) to reach 70 Bc at bottom hole circulating temperatures (BHCT) is illustrated in Table IV:

TABLE IV

| Ex. No. | BHCT (Deg F.) | R-12L-X2B | TT (HRS:MIN) to 70 Bc |
|---|---|---|---|
| 46 | 250 | 0.14 | 3:02 |
| 47 | 250 | 0.16 | 4:44 |
| 48 | 250 | 0.18 | 6:54 |
| 49 | 270 | 0.18 | 2:10 |
| 50 | 270 | 0.20 | 2:22 |
| 51 | 270 | 0.24 | 3:05 |
| 52 | 270 | 0.25 | 3:31 |
| 53 | 270 | 0.26 | 10:00 |
| 54 | 270 | 0.28 | 15:00 |
| 55 | 290 | 0.24 | 2:05 |
| 56 | 290 | 0.26 | 4:05 |
| 57 | 290 | 0.28 | 6:03 |
| 58 | 310 | 0.25 | 4:15 |
| 59 | 310 | 0.28 | 4:33 |
| 60 | 310 | 0.31 | 7:06 |
| 61 | 330 | 0.27 | 2:54 |
| 62 | 330 | 0.3 | 4:37 |
| 63 | 330 | 0.33 | 6:48 |
|  | 350 | 0.32 | 3:57 |
| 65 | 350 | 0.34 | 4:27 |
| 66 | 350 | 0.37 | 4:39 |
| 67 | 350 | 0.4 | 6:25 |
| 68 | 370 | 0.36 | 3:24 |
| 69 | 370 | 0.39 | 3:45 |
| 70 | 370 | 0.44 | 4:23 |
| 71 | 390 | 0.4 | 2:53 |
| 72 | 390 | 0.44 | 2:59 |
| 73 | 390 | 0.8 | 4:38 |
| 74 | 410 | 0.4 | 2:11 |
| 75 | 410 | 0.44 | 2:18 |
| 76 | 410 | 0.6 | 2:47 |
| 77 | 410 | 0.8 | 2:58 |

Figure 2:
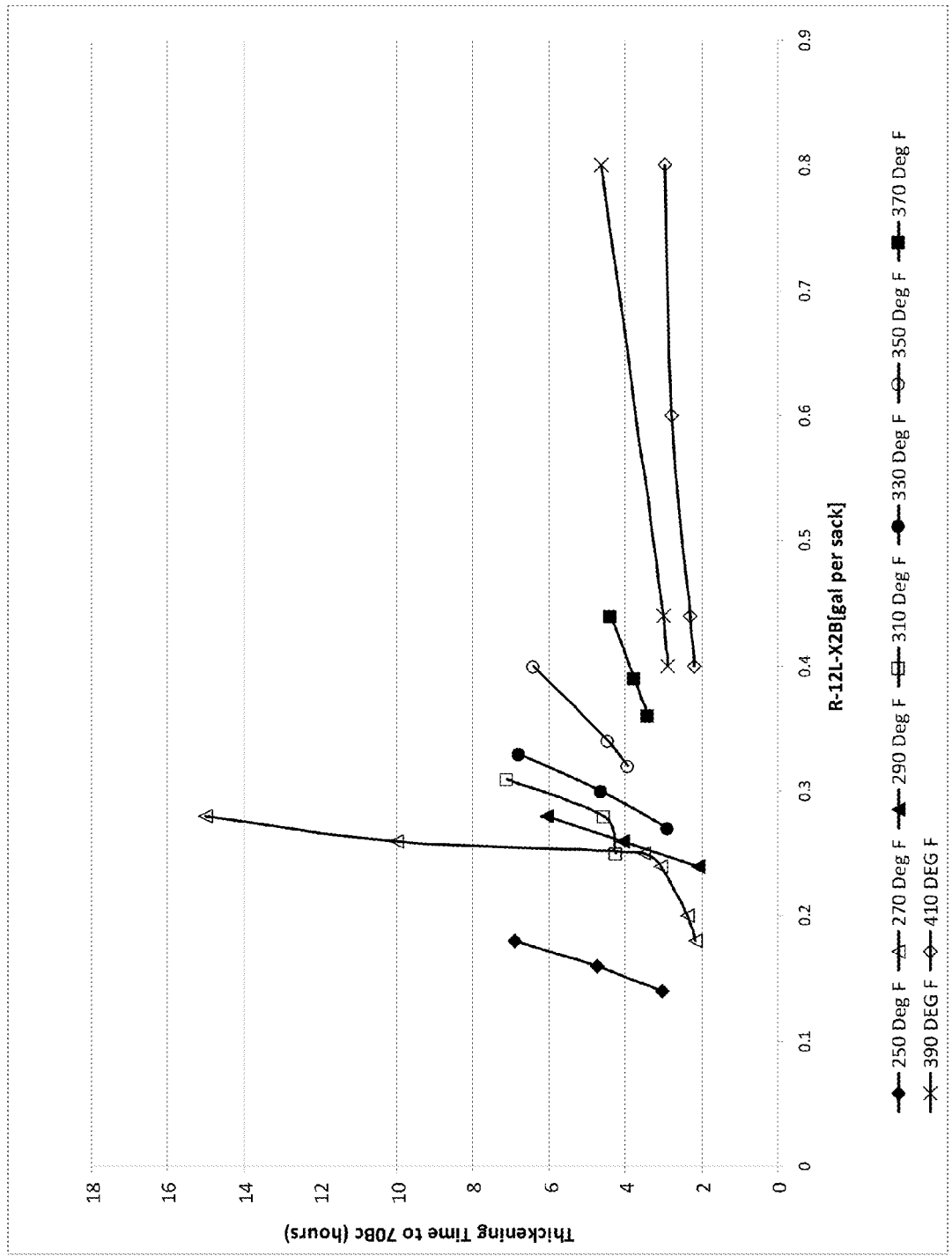
FIG. 2 shows the linear relationship of a boron/mono-glucoheptonate complex at temperatures up to 410° F.

Table IV illustrates that at temperatures as high as 410° F. control of the slurry setting remains possible. Further, Table IV shows that changing the molar ratio of polyhydroxy groups:boron from 2:1 to 1:1 reduces the breakdown point of 290° F. to 270° F. but increases the thermal stability of the glucoheptonate/borate complex up to 410° F. (slope of line approaches zero) of the complex as shown in FIG. 2. This means that at 410° F. and above, further retardation is not possible, regardless of how much retarder is added.

From the foregoing, it will be observed that numerous variations and modifications may be effected without departing from the true spirit and scope of the novel concepts of the invention.

What is claimed is:

1. A method of retarding hardening time of a cementitious slurry introduced into a wellbore, comprising:
   (a) introducing into the wellbore a cementitious slurry comprising water, a cement and a cement retarder, the cement retarder comprising a borate ester complex formed from a polyhydroxy compound and a borate salt in the presence of caustic, the molar ratio of the polyhydroxy compound to boron in the borate ester complex being between from 1:1 to about 4:1;

(b) disassociating the borate salt and the polyhydroxy compound from the borate ester complex at an elevated temperature to form a disassociated product; and (c) allowing the slurry to harden to a solid mass.

2. The method of claim 1, wherein the polyhydroxy compound is a sugar or a salt thereof.

3. The method of claim 2, wherein the sugar is gluconic acid, gluconate or glucoheptonate or a salt thereof.

4. The method of claim 3, wherein the sugar is gluconic acid or a salt thereof.

5. The method of claim 4, wherein the molar ratio of gluconic acid or salt to borate salt in the disassociated product is 2:1.

6. The method of claim 3, wherein the sugar is a sodium salt of glucoheptonate.

7. The method of claim 6, wherein the molar ratio of the sodium salt of glucoheptonate to borate salt in the disassociated product is 1:1.

8. The method of claim 6, wherein the molar ratio of the polyhydroxy compound to boron in the borate ester complex is 4:1.

9. The method of claim 1, wherein the cement retarder further comprises a lignin sulfonate.

10. The method of claim 9, wherein the weight ratio of lignin sulfonate to the borate ester complex is about 2:1.

11. The method of claim 9, wherein the lignin sulfonate is selected from the group consisting of sodium lignosulfonate and calcium lignosulfonate.

12. The method of claim 1, wherein the borate ester complex contains boron and di-glucoheptonate.

13. The method of claim 1, wherein the borate salt and the polyhydroxy compound disassociate from the borate ester complex at approximately 290° F.

14. The method of claim 1, wherein the borate salt is a metaborate.

15. The method of claim 14, wherein the borate salt is sodium metaborate.

16. The method of claim 1, wherein hardening of the cementitious slurry into cement is retarded until the temperature is in excess of 350° F.

17. The method of claim 16, wherein the hardening of the cementitious slurry into cement is retarded until the temperature is in excess of 400° F.

18. The method of claim 1, wherein the borate salt is sodium tetraborate and further wherein the molar ratio of caustic to sodium tetraborate is from about 1:1 to about 10:1.

19. The method of claim 1, wherein the Bearden consistency of the cementitious slurry of step (a) is between from about 2 to 20 Bc.

20. The method of claim 19, wherein the Bearden consistency of the cementitious slurry of step (a) is from about 5 to 11 Bc.

21. A method of cementing a casing within a gas or oil well, comprising:

(a) pumping into a gas or oil well a cementitious slurry comprising water, a hydraulic cement and a cement retarder, the cement retarder comprising a borate ester complex derived from a sugar or a salt thereof and sodium borate as a source of boron, the molar ratio of the sugar or salt thereof to boron in the borate ester complex being from 1:1 to about 4:1, and wherein the cementitious slurry is prepared by forming a first slurry of hydraulic cement and water and then adding the borate ester complex to the first slurry;

(b) disassociating the sodium borate and the sugar or salt thereof from the borate ester complex at a temperature of approximately 270° F. or above; and (c) cementing the casing with the gas or oil well by allowing the slurry to harden to a solid mass.

22. The method of claim 21, wherein the borate ester complex is prepared in the presence of caustic.

23. The method of claim 21, wherein the cement retarder further comprises a lignin sulfonate.

24. The method of claim 23, wherein the lignin sulfonate is selected from the group consisting of sodium lignosulfonate and calcium lignosulfonate.

25. The method of claim 21, wherein the borate ester complex is derived from either (a) boron and a di-gluconate, (b) boron and a mono-glucoheptonate, (c) boron and a di-glucoheptonate or (d) boron and a mono-gluconate.

26. The method of claim 21, wherein the sugar is gluconic acid, gluconate or glucoheptonate or a salt thereof.

27. The method of claim 26, wherein the sugar is a sodium salt of glucoheptonate and further wherein the molar ratio of the sodium salt of glucoheptonate to boron in the borate ester complex is 1:1.

28. A method of preventing over-retarding of a cementitious slurry during cementing within a gas or oil well, comprising:

(a) pumping into a gas or oil well a cementitious slurry comprising water, a hydraulic cement and a cement retarder, the cement retarder comprising a borate ester complex of either (a) boron and a di-gluconate, boron and a mono-glucoheptonate, boron and a di-glucoheptonate or boron and a mono-gluconate, and wherein the cementitious slurry is prepared by forming a first slurry of hydraulic cement and water and then adding the borate ester complex to the first slurry;

(b) disassociating a borate salt from the borate ester complex at temperatures of 270° F. and above and then releasing the borate salt into the cementitious slurry wherein over-retarding of the cementitious slurry is prevented by disassociation of the borate salt from the borate ester complex.

29. The method of claim 28, wherein the borate ester complex is prepared in the presence of caustic.

30. The method of claim 28, wherein the cement retarder further comprises a lignin sulfonate.

31. The method of claim 28, wherein the borate salt is a metaborate salt.

32. The method of claim 28, wherein the Bearden consistency of the cementitious slurry of step (a) is from about 5 to 11 Bc.

\* \* \* \* \*